(12) United States Patent
Rothschild et al.

(10) Patent No.: US 8,442,186 B2
(45) Date of Patent: May 14, 2013

(54) BACKSCATTER ENERGY ANALYSIS FOR CLASSIFICATION OF MATERIALS BASED ON POSITIONAL NON-COMMUTATIVITY

(75) Inventors: Peter Rothschild, Newton, MA (US); Ming Zhang, Wayland, MA (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 13/368,610

(22) Filed: Feb. 8, 2012

(65) Prior Publication Data
US 2012/0201356 A1 Aug. 9, 2012

Related U.S. Application Data

(60) Provisional application No. 61/440,491, filed on Feb. 8, 2011.

(51) Int. Cl.
*G01N 23/201* (2006.01)
(52) U.S. Cl.
USPC .................................. 378/86; 378/57; 378/87
(58) Field of Classification Search .............. 378/57, 378/62, 89–90, 146; 382/132
See application file for complete search history.

(56) References Cited

U.S. PATENT DOCUMENTS

| | | | |
|---|---|---|---|
| 6,151,381 A * | 11/2000 | Grodzins et al. | 378/90 |
| 6,249,567 B1 | 6/2001 | Rothschild et al. | 378/88 |
| 6,459,764 B1 | 10/2002 | Chalmers et al. | 378/88 |
| 7,072,440 B2 | 7/2006 | Mario et al. | 378/57 |
| 7,110,493 B1 | 9/2006 | Kotowski et al. | 378/87 |
| 7,409,042 B2 | 8/2008 | Bertozzi et al. | 378/88 |
| 7,561,666 B2 | 7/2009 | Annis | 378/87 |
| 7,593,506 B2 | 9/2009 | Cason | 378/90 |
| 2009/0168958 A1* | 7/2009 | Cozzini et al. | 378/57 |
| 2009/0268871 A1 | 10/2009 | Rothschild et al. | 378/87 |

OTHER PUBLICATIONS

Harding, et al., "Dual-Energy Compton Scatter Tomography," *Phys. Med. Biol.*, vol. 31, pp. 477-489, (1989).
Korean Intellectual Property Office, Officer Hosoon IM, International Search Report and Written Opinion, PCT/US2012/024248, date of mailing Jul. 9, 2012, 10 pages.

* cited by examiner

*Primary Examiner* — Hoon Song
*Assistant Examiner* — Mona M Sanei
(74) *Attorney, Agent, or Firm* — Sunstein Kann Murphy & Timbers LLP (57) ABSTRACT

A system and methods for characterizing regions within, or on, an inspected object, wherein a lower-Z scattering material and a higher-Z material may both lie along a common line of sight. The inspected object is scanned with penetrating radiation characterized by an energy distribution, and penetrating radiation scattered by the inspected object is detected in a manner that generates two detector signals that distinguish between materials of higher and lower effective atomic number under distinct sets of conditions with respect to the energy distribution of the penetrating radiation. An image is generated, based on a function of the two detector signals, as is a differential image, so as to allow distinction of higher-Z and lower-Z materials.

10 Claims, 6 Drawing Sheets

BACKSCATTER ENERGY ANALYSIS FOR CLASSIFICATION OF MATERIALS BASED ON POSITIONAL NON-COMMUTATIVITY

The present application claims the priority of U.S. Provisional Patent Application 61/440,491, filed Feb. 8, 2011, and incorporated herein by reference.

TECHNICAL FIELD

The present invention relates to systems and methods for classifying materials as to their effective atomic numbers based on detection of penetrating radiation scattered therefrom.

BACKGROUND ART

Backscatter x-ray inspection systems have been used for more than 25 years to detect organic materials concealed inside baggage, cargo containers, in vehicles, and on personnel. Because organic materials in bulk preferentially scatter x-rays (by Compton scattering) rather than absorb them, these materials appear as brighter objects in backscatter images. However, because the backscatter intensity is a complicated function of the distance, position, and the shape and thickness of the object, as well as the amount of intervening clutter obscuring the object, it is difficult to use the backscatter intensity to further classify the organic material.

Simulations carried out over many years have attempted to find a reliable way of using dual-energy (or multi-energy) backscatter measurements to assist in identifying concealed materials, other than by just using the measured intensity alone. One method is to alternate the energy of the x-ray source, and to look at the relative backscatter intensity from an object in the backscatter image at the two energies. The ratio R of the low energy intensity to the high energy intensity of backscattered x-rays can be used to classify the object material. Another method is to use a single energy source, but to temporally change the beam filtration so that beams with alternating energy spectra are incident on the object being inspected. Examples are taught, for example, in U.S. Pat. No. 6,249,567 (to Rothschild, et al.) and U.S. Pat. No. 6,459,764 (to Chalmers, et al.), both of which are incorporated herein by reference.

A further method known in the art for illuminating an inspected object with multiple energies is to use a single energy source, and energy-resolving detectors, whereby the energy of each backscatter x-ray photon is characterized when it is detected. In this case, the ratio R may be defined as the detected intensity in an energy range with a lower average energy divided by the intensity in an energy range with a higher average energy.

In each of the foregoing scenarios, it can be shown that the ratio R is a strong function of the distance from the detectors to the illuminated object and a somewhat weaker function of the shape of the illuminated object. This is because the energy of backscattered x-rays depends strongly on the scatter angle, whose range in this case is defined by the solid angle of the detectors relative to the point of scatter. Since the solid angle is a function of the distance D between the detectors and the scatter point, the ratio R is also a function of the distance D. Moreover, since the detectors are typically offset from the beam plane by some distance, the amount of overlying material within the object that the scattered radiation must pass through (from the scatter point to the detectors) also depends on the distance to the object. This effect is very noticeable in a flat sheet of steel, for example, where for an incident 225 kV Bremstrahlung beam, the mean energy of the scattered x-rays incident on the detectors (offset from the beam axis by 12 inches) can vary from 72 keV for scatter from an object a few feet away to only 63 keV for an object at a distance of 10 feet. This means the scattered radiation from a sheet of steel close to the detectors is significantly hardened compared with scattered radiation from a more distant steel sheet.

The dependence of the ratio R on the shape of the illuminated object is due to the varying path length inside the object that the scattered x-rays must traverse before exiting the object and reaching the detectors. For example, this distance is smaller for spherical objects compared with rectangular ones. For objects consisting of higher-Z material (which preferentially absorbs the lower energy x-rays), this will result in a lower value of R for the rectangular objects compared with the spherical ones.

Consequently, a reliable mechanism for using energy resolution of x-ray backscatter properties of an object to classify the object by atomic number has proven elusive.

The general concept of using energy analysis of backscattered x-rays to screen personnel, where the energy spectrum of the x-ray source beam is varied over time by a periodically varying filter, has been taught in U.S. Pat. No. 7,561,666 (to Annis, incorporated herein by reference), however the teachings of Annis are restricted to the case where the scattering object is not screened by an intervening layer of highly attenuating material, while screening by a high-Z material is generally the case where materials are screened in a metal suitcase or a vehicle. At the typical x-ray energies at which x-ray backscatter body scanners operate, 40-110 keV, the classification of materials is necessarily quite crude, with all objects being classified into one of only three or four ranges of atomic number. These might include organic, aluminum, metallic (e.g. steel or copper, etc.), and high-Z (e.g. lead) materials. Typically, moreover, the relative brightness of the backscatter signal is already capable of providing adequate separation between these categories of materials for body scanners, and the energy resolution of the backscatter signal is superfluous.

What would be more useful would be to be able to discriminate between different organic materials—for example, between human tissue and explosives. However, if this is to be accomplished using the techniques taught by Annis, the endpoint energy of the lower energy must be very low (only about 30 keV or less), making the practical application of this technique problematic for a practical body scanner, because of the high attenuation of x-rays in this energy range by intervening clothing between the x-ray source and the inspected person's body.

Moreover, the teachings of Annis nowhere address the question of whether highly scattering objects, such as organic materials, lie in front of, or behind, a highly attenuating structural feature such as a sheet of high-Z material, such as a steel car body, for example.

DEFINITION

As used herein, and in any appended claims, the term "placement" used in the context of a material within an inspected object shall refer to the relative distance of that material from a fiducial reference position such as the source of the primary illuminating x-ray beam.

SUMMARY OF EMBODIMENTS OF THE INVENTION

In accordance with various embodiments of the present invention, methods are provided for characterizing regions within an inspected object wherein a lower-Z scattering material and a higher-Z material may both lie along a common line of sight. The methods have steps of:

a. scanning the inspected object with penetrating radiation emitted by a source characterized by an energy distribution;

b. detecting penetrating radiation scattered by the inspected object in a manner generating a first detector signal that distinguishes between materials of higher and lower effective atomic number under a first set of conditions with respect to the energy distribution of the penetrating radiation;

c. detecting penetrating radiation scattered by the inspected object in a manner generating a second detector signal that distinguishes between materials of higher and lower effective atomic number under a second set of conditions with respect to the energy distribution of the penetrating radiation;

d. generating a differential image based on a function of the first and the second detector signals; and e. determining placement of materials of lower Z and higher Z within the single line of sight relative to the source, based at least on the differential image.

In accordance with other embodiments of the present invention, scanning the inspected object with penetrating radiation may entail sequentially scanning the inspected object with penetrating radiation characterized by a first energy distribution and a second energy distribution. There may also be a step of ascertaining relative placement of a lower-atomic number region with respect to a higher-atomic number region within an inspected object based at least on values of respective regions within the differential detector image, based, optionally, in whole or in part, on segmentation. The penetrating radiation employed in accordance with embodiments of the present invention may be x-ray radiation.

In accordance with alternate embodiments of the present invention, a system may be provided for characterizing regions within an inspected object. The system has a source of penetrating radiation for generating a beam of penetrating radiation and a scanner for scanning the penetrating radiation across the inspected object. The system also has an energy discriminating means for distinguishing scattered penetrating radiation detected under a first set of conditions with respect to an energy distribution of scattered radiation and a second set of conditions with respect to an energy distribution of scattered penetrating radiation. Finally, the system has an image generator for generating a first image based on a function of the radiation detected under only one of the first and second set of conditions with respect to the energy distribution and a difference image generator for generating a differential image based on a function of the radiation detected during the first set of conditions and the radiation detected during the second set of conditions with respect to the energy distribution.

In further embodiments of the present invention, the energy discriminating means may include a first detector characterized by a first response distribution as a function of detected energy and a second detector characterized by a second response distribution as a function of detected energy. The source of penetrating radiation may be an x-ray tube.

In yet further embodiments of the present invention, the first and second detectors may be disposed either on respective sides of the source of penetrating radiation, or else the first and second detectors are disposed on each side of the source of penetrating radiation.

BRIEF DESCRIPTION OF THE FIGURES

The foregoing features of the invention will be more readily understood by reference to the following detailed description, taken with reference to the accompanying figures, in which.

DETAILED DESCRIPTION OF EMBODIMENTS OF THE INVENTION

Definitions

As used in this description, and in any appended claims, the terms "high-Z" and "low-Z" shall have connotations relative to each other, which is to say that "high-Z" refers to a material, or to a line of sight, characterized by an effective atomic number Z that is higher than a material or line of sight referred to, in the same context, as "low-Z".

For heuristic convenience, "Z", unless otherwise specified or required by context, shall refer to the "effective atomic number" characterizing a region of a heterogeneous material comprising multiple elements. The "effective atomic number" is the average atomic number, where the average is of a type commonly employed in x-ray-matter interactions.

As used in this description and in the appended claims, the term "image" refers to any multidimensional representation, whether in tangible or otherwise perceptible form or otherwise, whereby a scalar value of some characteristic is associated with each of a plurality of locations corresponding to dimensional coordinates of an object in physical space, though not necessarily mapped one-to-one thereonto. Examples of such characteristics include the level of a detector signal or a scalar function of detector signal levels. Additionally, for example, the graphic display of the spatial distribution of some feature, such as atomic number, in one or more colors constitutes an image. So, also, does an array of numbers in a computer memory or holographic medium. Similarly, "imaging" refers to the rendering of a stated physical characteristic in terms of one or more images.

As used in this description and in the appended claims, the term "function" as applied to multiple variables is used in the broadest mathematical sense, to include linear or nonlinear combinations of the variables, whether the function is analytical, or otherwise, continuous, or otherwise, differentiable, or otherwise, or whether the function is derived from a lookup table. A function of multiple variables may have no dependence upon one or more of the variables.

As used in claims appended hereto, the term "value" associated with a pixel shall refer to the scalar value of a specified quantity or characteristic to which an image refers. Thus, such a "value" might quantitatively represent a scaled brightness of a scatter signal associated with that pixel, or it might be a value that is a function of one or more measured quantities. A "value" may also be associated with a region or subregion, in which case the term refers to an average of the values of pixels of an image associated with that region or subregion. The average may be a weighted average, and is not restricted to an arithmetic average, or to any particular type of average.

As used herein, and in any appended claims, the term "difference image" refers to an image obtained by combining the results of sensing using two distinct modalities referenced to the same imaged space. The combination may be by subtraction (rendering a "pure difference image") or by another form of linear combination, or, otherwise, by non-linear combination, or by combination of any sort of values associated, respectively, with each sensing modality. Thus, for example, a look-up table may be used to generate a difference image based on a first value associated with a particular pixel, or region of pixels, as sensed using a first modality, and a second value associated with the a corresponding pixel, or region of pixels, as sensed using a second modality.

While the description provided herein refers to "backscatter" alone, as a matter of heuristic convenience, it is to be understood that the apparatus and techniques described herein may be practiced with scatter directed in directions other than backward with respect to the propagation direction of an incident beam of penetrating radiation. Use of the apparatus and techniques described herein with respect to scatter in any direction whatsoever is within the scope of the present invention and any claims appended hereto.

Energy distributions of penetrating radiation may be denoted herein, as a matter of notational convenience, by reciting their terminal emitted energy (often called the "endpoint" energy). Thus, for example, an x-ray tube emitting Bremsstrahlung radiation due to electrons accelerated through a potential of 100 kV, will emit x-rays of energy less than 100 keV, and the spectrum of emitted radiation may be characterized, herein, as a "100 keV beam," and an image of detected radiation scattered from that beam may be referred to herein as a "100 keV scatter image."

Description of Embodiments

While, as a matter of convenience, embodiments of the present invention may be described herein in terms of energy resolution following interaction of penetrating radiation with the inspected object (i.e., using detectors with differential energy sensitivity or detectors with energy resolution), it is to be understood that varying the energy spectrum of the incident beam, either by varying the spectrum of a single source (for example, by changing the end point energy, or the beam filtration, or otherwise), or by employing multiple sources, is equally within the scope of the present invention.

Figure 1:
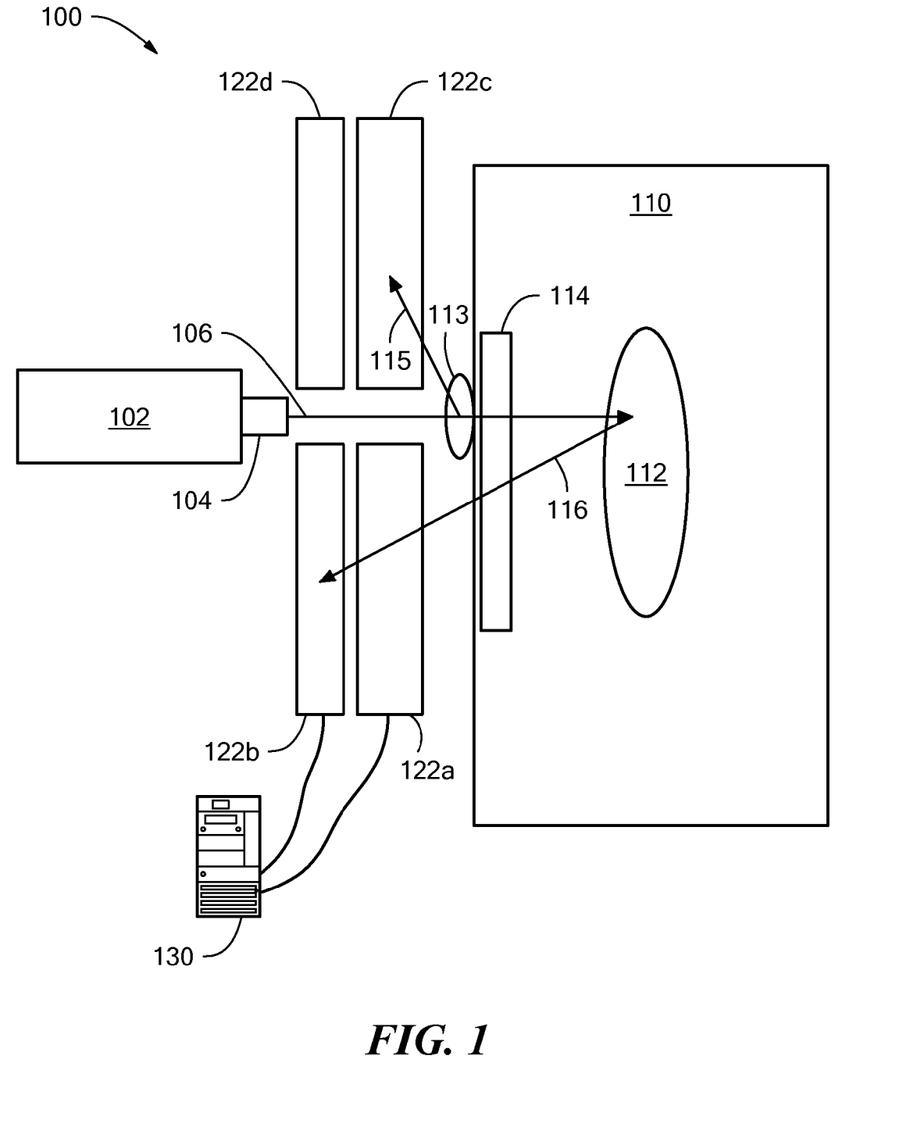
FIG. 1 is a schematic depiction of a multiple-energy backscatter system in accordance with embodiments of the present invention.

A system in accordance with embodiments of the present invention is now described with reference to FIG. 1. A multiple-energy backscatter system, designated generally by numeral 100, is employed to characterize an inspected item 110, which may be vehicle, for example, or may be an item of cargo, etc. A source 102 of penetrating radiation such as an x-ray tube emits penetrating radiation formed into a beam 106 by collimator 104 which may also serve to modulate beam 106 in other ways such as temporally or spectrally. Beam 106 impinges upon scattering material 112 within inspected item 110 after traversing higher-Z material 114, which may be the steel body of a vehicle, for example. Sometimes, beam 106 will first impinge, along a line of sight, upon a lower-Z material 113 that overlays higher-Z material 114. Interaction with scattering material 112 gives rise to scattered penetrating radiation 116, some of which is intercepted by one or more of scatter detectors 122a-122d. Scatter detectors 122a-122d may have distinct spectral sensitivities, for example, detectors 122b and 122d may preferentially detect higher-energy detectors that have traversed detectors 122a and 122c. Similarly, overlaying material 113 similarly gives rise to backscattered radiation 115, again detected by scatter detectors 122a-122d. It is to be understood that all real materials give rise to Compton scattering of photons, such that higher-Z material 114 scatters as well. However, due to lower self-absorption of scattered radiation within lower-Z material, it is lower-Z material, such as organic material, for example, which typically gives rise to brighter (more intense) scatter signals, in practical situations. Scatter signals generated by scatter detectors 122a-122d upon detection of scattered penetrating radiation 115 and 116 are coupled to processor 130 which processes the signals as further described below generating images which may be displayed, as also discussed below.

In other embodiments of the invention, as discussed below, incident beam 106 of penetrating radiation may be characterized by a spectrum that varies with time, such as to constitute a spectrum of higher average energy during a portion of a cycle, and a spectrum of lower average energy during another portion of a cycle. A backscatter signal associated either with a detector with greater sensitivity to higher energy, either inherently or by virtue of timing of a time-variable source, may be referred to as a "higher-energy backscatter signal", and the detected radiation to which that signal corresponds may be referred to, herein, as "higher-energy backscatter." Mutatis mutandis, a backscatter signal associated either with a detector with greater sensitivity to lower energy, either inherently or by virtue of timing of a time-variable source, may be referred to as a "lower-energy backscatter signal", and the detected radiation to which that signal corresponds may be referred to, herein, as "lower-energy backscatter."

The value of the ratio R of the lower energy backscatter to the higher energy backscatter is a function not only of the distance from the detectors to the illuminated object, and of the shape of the object, but is also strongly dependent on the thickness and composition of any overlying material located between the illuminated object 112 and the x-ray source 102, and between the object 112 and the detectors 122a-122d. Organic overlying materials 113 will tend to reduce the intensity of the backscatter coming from the illuminated object 112, while leaving the value of R relatively unchanged. Higher-Z overlying materials 114, however, will preferentially absorb the lower energy components of the scatter, resulting in a lower value of R than if the illuminated object had no higher-Z overlying material.

Because of this last effect, dual-energy backscatter (or multiple-energy backscatter), in accordance with embodiments of the present invention, allows some degree of material classification in circumstances where the object being identified is the first to be illuminated by the x-ray beam and the backscatter from the illuminated object can reach the backscatter detectors without passing through any significant amounts of overlying materials. In addition, the object's distance and position relative to the backscatter detectors should preferably be known, so that the ratio R can be corrected accordingly. Knowledge of the distance and position of scatterer 112 relative to backscatter detectors 122a-122d may come to be known, within the scope of the present invention, using any means of position determination, including, for example and without limitation, concurrent x-ray transmission or sidescatter imaging, temporally resolved pulsed scatter measurements, scatter intensity analysis, millimeter-wave imaging, etc.

For most practical inspection applications, where materials of interest are concealed within some kind of outer enclosure 110 (for example, a suitcase or the side of a vehicle), the uncertainty hitherto discussed largely rules out the possibility of using dual energy (or multi-energy) backscatter analysis for material identification. The exceptions would be if bare explosives were used in an improvised explosive device (IED), without an intervening high-Z material, or if materials are concealed under the clothing of a person. In this latter case, the person's clothing interacts only weakly with the x-ray beam, and the concealed material has the dominant influence on the spectral shape of the backscatter spectrum, as discussed in U.S. Pat. No. 7,561,666 (to Annis).

There is, however, an entirely distinct practical application that lends itself to the technique of backscatter energy analysis uniquely enabled by the present invention, namely, the ability of dual (or multi-energy) backscatter analysis to assist in the segmentation and/or filtering of features in backscatter images of vehicles or other objects, which, in turn, allows automatic threat detection algorithms to more accurately determine which features correspond to threat items as opposed to benign items.

A backscatter system, as may be employed, for example, for the inspection of personnel, is described in U.S. Pat. No. 7,809,109 (to Mastronardi, et al.), which is incorporated herein by reference. A backscatter system, as may be employed for the inspection of parcels and luggage is described in U.S. Pat. No. 7,555,099 (to Rothschild, et al.), which is incorporated herein by reference. A backscatter system, as may be employed for the inspection of vehicles is described in U.S. Pat. No. 7,593,506 (to Cason, et al.), which is incorporated herein by reference, as well. Configurations described in any of the foregoing systems lend themselves to multi-energy backscatter material analysis in accordance with embodiments of the present invention.

Figure 4A:
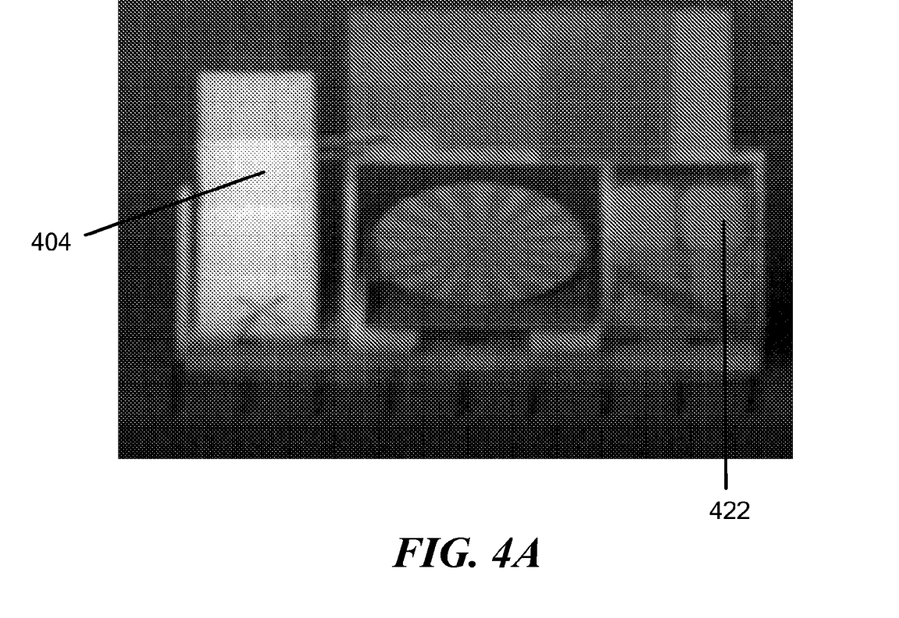
FIG. 4A depicts a regular 140 keV backscatter image of a test phantom acquired with a gadolinium oxy-sulfide (GOS) scintillator detector.
Figure 7:
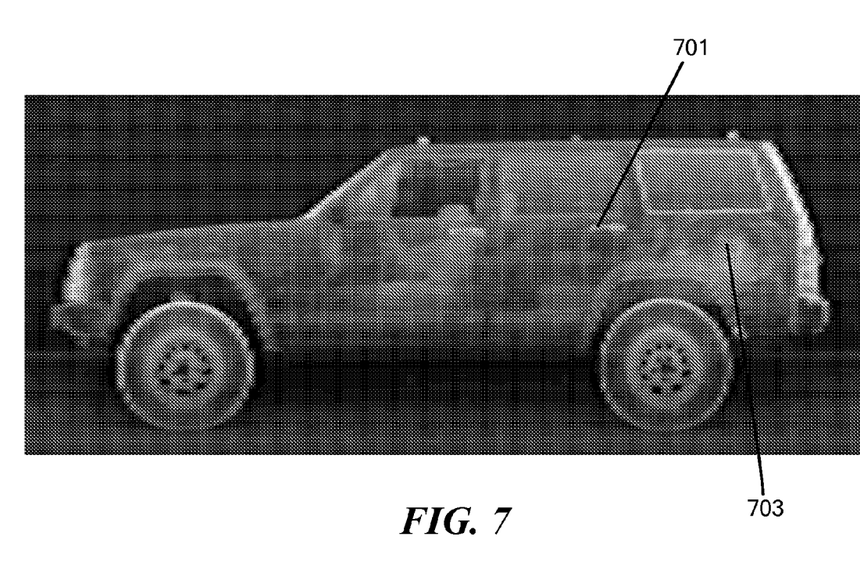
FIG. 7 is an x-ray backscatter image derived, in accordance with an embodiment of the present invention, showing higher scatter due to organic items on the outside of a vehicle and due to organic threat items concealed within the vehicle.

Threat items may be recognized by an operator to whom backscatter images, as shown in FIGS. 4A and 7, are presented on a display. Moreover, software Operator Assist algorithms may be employed to automate, in whole or in part, the process of identifying threat items. Operator Assist technology is taught in Ahmed et al., "Historical Comparison of Vehicles using Scanned X-Ray Images," presented at the *IEEE Workshop on Applications of Computer Vision*, Kona, Hi., Jan. 5-7, 2011, which paper is incorporated herein by reference.

Methods and apparatus in accordance with the present invention may be applied advantageously to the backscatter x-ray inspection of vehicles, for example. Operator Assist (OA) Algorithms that automatically look for threat items within the vehicle images must decide if brighter parts of the vehicle exhibiting higher scatter are due to organic items 701 on the outside of the vehicle (such as door handles, support structures for external mirrors, plastic molding, etc.) or due to organic threat items 703 concealed within the vehicle, as shown in FIG. 7. The absolute brightness of the backscatter from the inspected region cannot be used, as thin organic materials on the outside of the vehicle can have a similar brightness to thicker organic threats on the inside of the vehicle.

In the prior art, the distinction between organic items on the outside of a vehicle and such items on the inside of the vehicle was made based on the location of the bright regions relative to the segmented image of the vehicle. A segmentation algorithm divides the vehicle image into regions which represent the vehicle doors, tires, windows, etc. If a bright part of the image is located within these segmented regions at an expected position (for example, where the door handles are expected to appear within a door region), they will not be flagged as threats. The difficulty with this approach is the need to account for the large variation between different types and brands of vehicles, and the variation in location and backscatter intensity of the brighter regions.

In accordance with embodiments of the present invention, a distinction can be made between bright parts of the image corresponding to objects on the outside of a steel vehicle body, versus those on the inside without recourse to prior segmentation assumptions, but, rather, on the basis of whether a comparison of a single-energy image with a differential energy image indicates that a low-Z material lies within, rather than outside, a high-Z enclosure. Once low-Z materials outside the vehicle have been identified, it may then be assumed that any concealed threat on a vehicle will be on the inside of the steel body, allowing an operator assist algorithm to ignore all the bright parts of the vehicle that are identified as being due to objects on the outside. This greatly simplifies the OA algorithm—now only brighter parts in the image that are identified as being from objects on the inside of the vehicle need to be analyzed. Using the segmented vehicle image, the remaining bright parts of the image can be compared with the expected positions of benign scattering objects located within the vehicle body. These would include, for example, the driver and any passengers, and internal fluid reservoirs such as the windshield washer fluid. Note that one exception to this method would be threat items concealed behind the plastic bumpers of vehicles. In this case, the boundaries of the bumper regions can be determined from the segmented image, and these regions can then be analyzed with a different algorithm.

Figure 2:
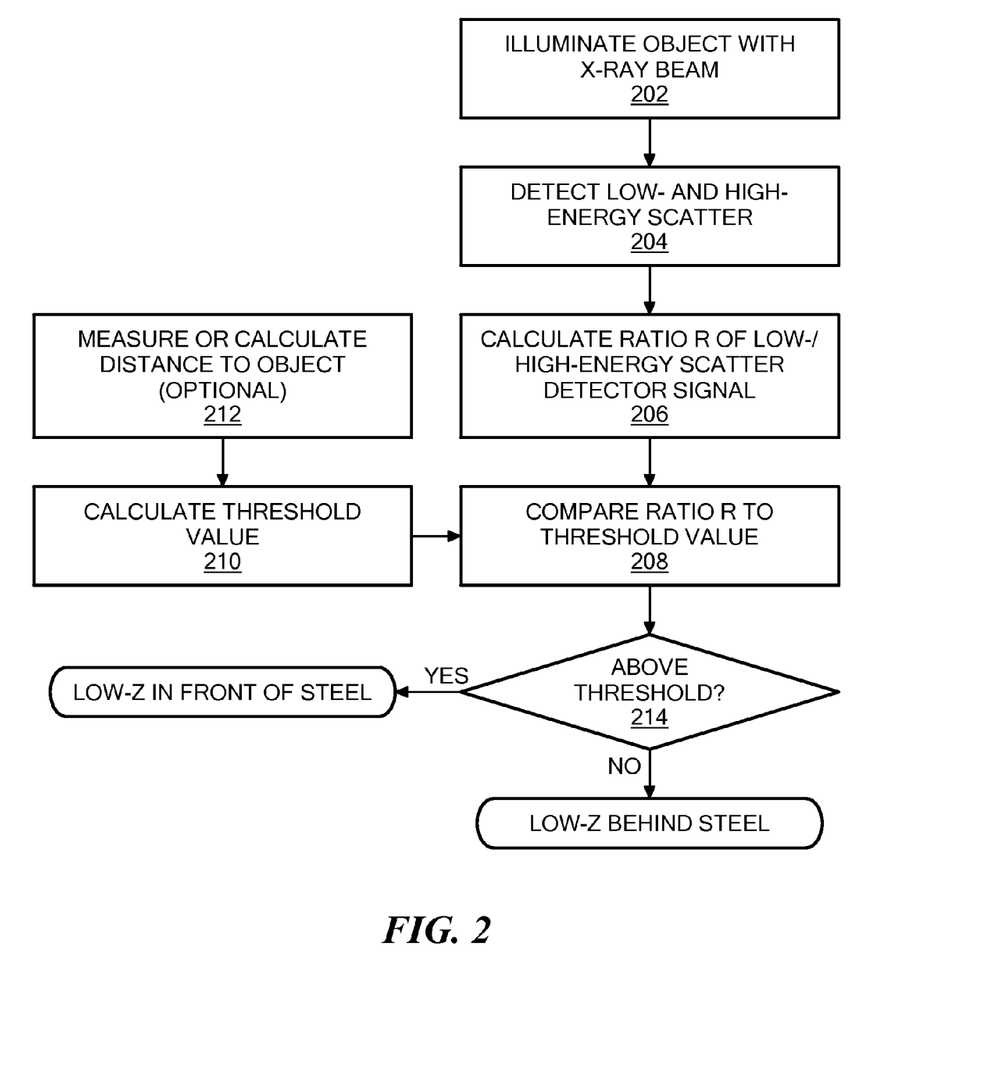
FIG. 2 is a flowchart depicting a scatter imaging process in accordance with certain embodiments of the present invention.

Methods in accordance with embodiments of the present invention are now described with reference to the flowcharts of FIGS. 2 and 3. FIG. 2 depicts a process wherein illumination 202 by an illuminating x-ray beam is performed with a substantially stationary spectrum. (It is to be understood that the source may be temporally modulated, within the scope of any embodiment of the present invention). In process 204, detection is performed using multiple scatter detectors, or otherwise, such that one signal preferentially registers high-energy scatter, while a second signal preferentially registers low-energy scatter. A ratio of the backscatter signal from the low- and high-energy scatter detection is calculated in process 206. It is to be understood that the term "ratio," as used herein, encompasses weighted or corrected ratios, logarithmic differences, etc.

Once the ratio of the low-energy to high-energy scatter signal has been calculated, it is compared (208) with a threshold value to determine whether the illuminated object is behind, or in front of, the high-Z barrier. It is to be understood that the inverse ratio may also be compared to a threshold. Note that the ratio is only one example of comparing the two backscatter signals, and any function of the two signals, whether linear or non-linear, can be used.

In preferred embodiments of the invention, the value of the ratio R is compared with the threshold value on a pixel-by-pixel basis in the image, allowing a determination to be made for every pixel in the image. In actual systems used for vehicle inspection, however, the x-ray intensity is typically insufficient to allow the value of R to be calculated for a single pixel to the required accuracy, due to the limited number of scattered photons that can be detected in the integration time of a single pixel. For this reason, a sub-region of the image consisting of many pixels (for example, a 10×10 pixel area) can be analyzed, and the value of R calculated from the summed backscatter signals from all the pixels in the subregion.

In different embodiments of the invention, the threshold value, against which ratio R is compared to determine whether lower-Z scatterer 112 (shown in FIG. 1) lies behind, or in front of higher-Z material 114 may be determined on an empirical basis and prescribed to processor 130, or may be adjusted by an operator, or may be calculated (in step 210) during the course of inspection, based on a measurement or calculation 212 of a distance to scatterer 112.

Figure 3:
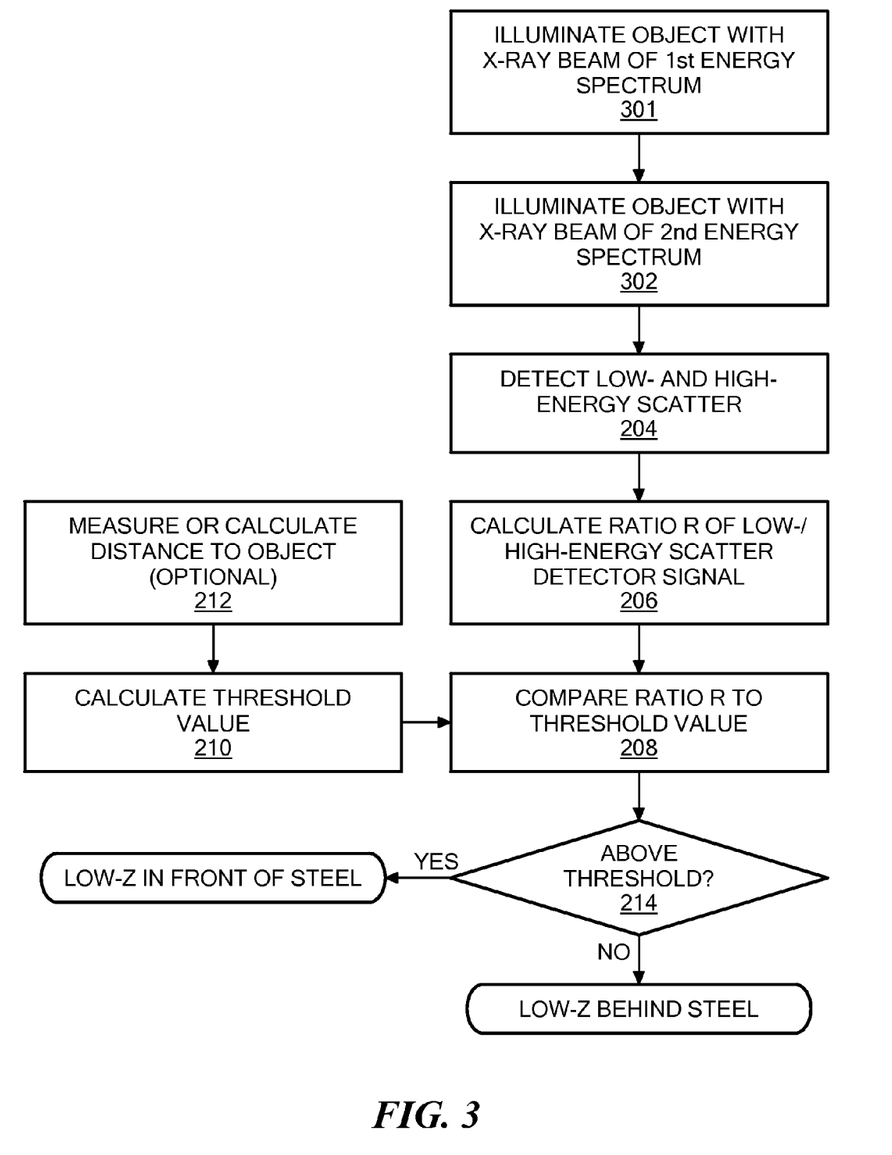
FIG. 3 is a flowchart depicting a scatter imaging process in accordance with other embodiments of the present invention.

Referring, now, to FIG. 3, a flowchart of a process is depicted that parallels that shown in FIG. 2, except that in this case the energy of the x-ray beam is temporally modulated (for example, by varying the end-point energy or varying the beam filtration), rather than relying on the differential energy sensitivity of the scatter detectors.

Demonstration of Operation in Accordance with Embodiments of the Invention

Results are presented based on dual energy backscatter imaging tests using a single energy x-ray source 102 and a pair of detectors 122a and 122c located on each side of the x-ray source. One of the detectors used is a barium fluorochloride (BFC) scintillation detector, which has a k-edge for the barium at 37.4 keV. The second detector used a gadolinium oxy-sulfide (GOS) scintillator, with the gadolinium having a k-edge at 50.2 keV. The BFC detector is, therefore, more sensitive for detecting lower energy x-rays than the gadolinium detector, and exhibits relatively higher detection signals for scatter from organic materials than the GOS detector, while the BFC detector exhibits relatively lower signals than the GOS detector from high atomic number (metallic) materials.

Figure 4B:
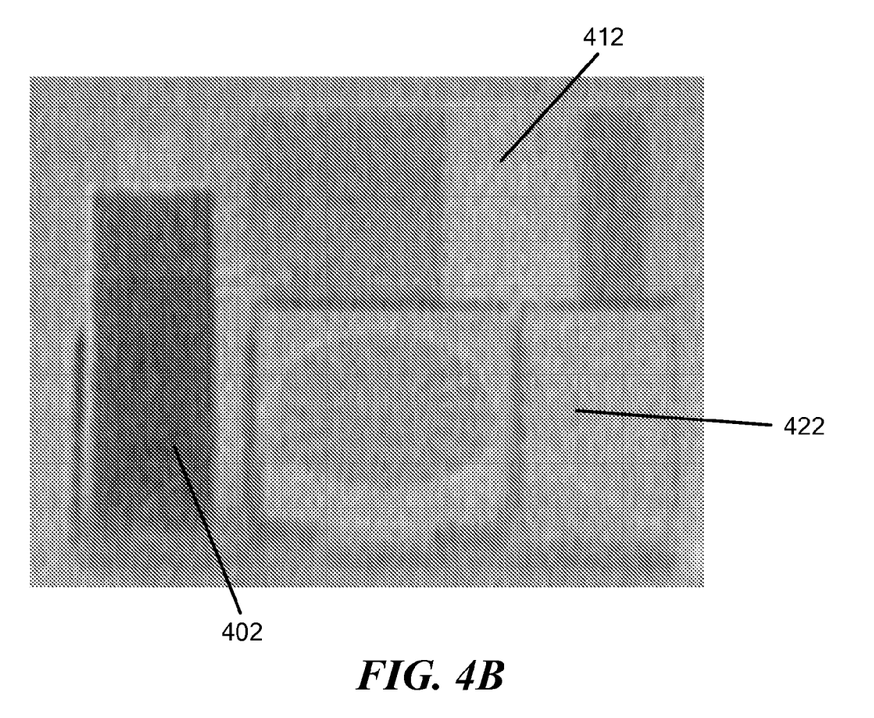
FIG. 4B depicts a difference image obtained by subtracting a backscatter image of the same phantom acquired with a barium fluoro-chloride (BFC) scintillator from the GOS image of FIG. 4A.

The differential response of BFC to GOS detection may be observed in FIGS. 4A and 4B. FIG. 4A is a 140 keV backscatter image acquired with a GOS detector, while FIG. 4B is a normalized difference backscatter image (GOS-BFC) of the identical scene. The signals from the two detectors are weighted so that organic regions 402 in the difference image (FIG. 4B) appear dark (unlike the regular backscatter images, where they appear as bright regions 404). This implies that high-Z regions 412 will appear brighter in the difference image (FIG. 4B), as the BFC signal is smaller than the GOS signal for these regions. Areas of unconcealed plastic and steel appear dark and bright, respectively, in the difference image. However, sugar packages 422 in the lower right hand corner remain bright in the difference image because they are concealed behind a thin steel sheet.

FIGS. 4A and 4B, thus, illustrate both applications of energy-specific backscatter described herein. Unconcealed materials are either bright 412 (indicative of high-Z material) or dark 402 (indicative of low-Z) in the difference image (FIG. 4B), depending on their atomic number. However, organic materials concealed behind steel (e.g., the packages of sugar 422 in the lower right hand corner of FIG. 4A) also appear bright in the difference image (FIG. 4B), in accordance with the second application of energy-specific backscatter described herein. Comparison of FIGS. 4A and 4B, for example, allows for determination as to whether organic materials that appear relatively bright in the regular backscatter image are behind (bright in both images), or in front of (bright in FIG. 4A and dark in FIG. 4B) steel, or other high-Z material. Thus, the placement of a low-Z material in relation to a high-Z material is non-commutative with respect to its appearance in the combination of a backscatter image such as FIG. 4A and a difference image such as FIG. 4B.

Figure 5A:
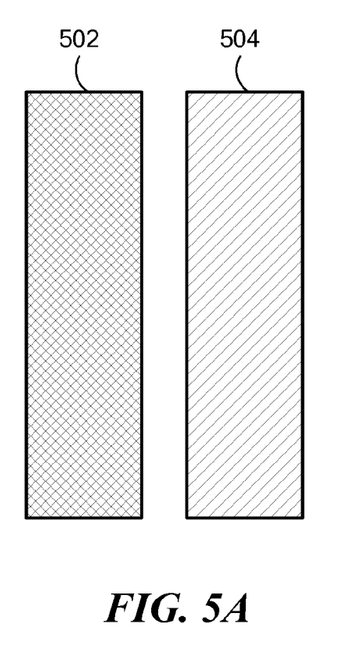
FIGS. 5A and 5B schematically depict alternate scatter detector configurations in accordance with embodiments of the present invention.

Other embodiments of the invention are now described with reference to FIGS. 5A and 5B. In embodiments in accordance with both FIGS. 5A and 5B, source 102 (shown in FIG. 1) is located above the plane of the page, such that beam 106 is directed into the page. In FIG. 5A, a backscatter detector 502 to the left of the x-ray source 102 is more responsive to low-energy backscatter than a second backscatter detector 504 to the right of the x-ray source 102. An example of this is to use two BFC detectors, with the right detector 504 having a front filter through which the scattered x-rays must pass before detection. Typical choices for the filter for a 225 kV x-ray source could be 0.5 mm thick iron, 0.2 mm thick tin, or 0.75 mm thick copper. The ratio R of the unfiltered to filtered detector signals can be used to characterize each pixel in the backscatter image.

A deficiency of the detector configuration shown in FIG. 5A is that the scatter radiation 115 and 116 (shown in FIG. 1) incident on the front face of the two detectors could be quite different due to shadowing or absorption effects in the item (or object) 110 being scanned. For example, the shape of the object might mean that the scattered x-rays must pass through more overlying material to reach the left (unfiltered) detector 502 than the right (filtered) detector 504. This would cause the ratio R to have a value lower than it would otherwise have, possibly resulting in the scattering object 113 being erroneously assigned to being behind, instead of in front, of the steel higher-Z object 114.

Figure 5B:
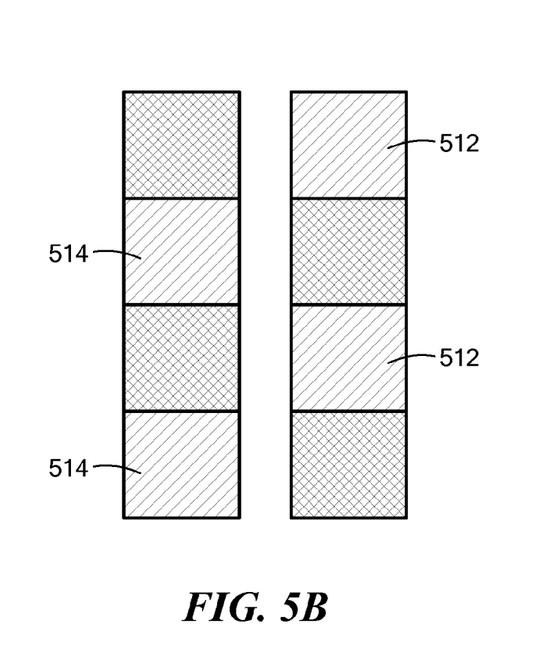

A preferred detector configuration is shown in FIG. 5B. In this configuration, both filtered 514 and unfiltered 512 detectors are positioned on either side of the x-ray source 102, which greatly reduces the impact of any shadowing or absorption effects, as the aforementioned effects influence both the filtered and unfiltered detector elements equally.

Figure 6:
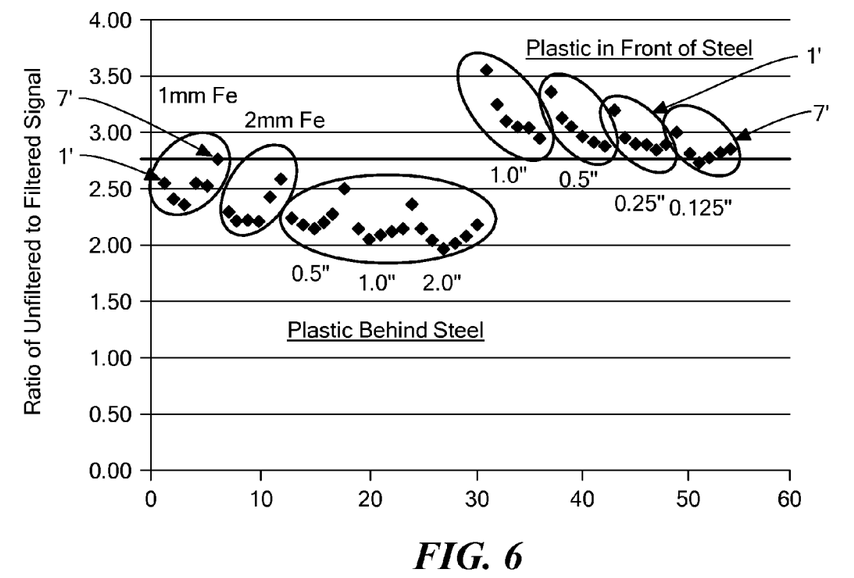
FIG. 6 shows the value of the unfiltered to filtered backscatter detector segments for scatter off plastic located behind, and in front of, 1 mm thick steel.

Simulations were carried out for a 225 kV beam illuminating plastic targets of varying thickness behind 1 mm thick steel, at distances of 1 to 7 feet. The detectors consisted of BFC in the configuration shown in FIG. 5B, with 0.75 mm thick copper on the filtered detector elements. The results are shown in FIG. 6. It can be seen that if a threshold of R=2.75 is used, pixels in the image corresponding to scatter from plastic in front of the steel can be separated from scatter coming from the bare steel, or from organic material concealed behind the steel. This confirms, for example, that the detector geometry depicted in FIG. 5B enable an operator assist algorithm, based on segmentation, as previously described, to sort bright regions in the image as being from features internal to, or features external to, the steel body of a vehicle.

The described embodiments of the invention are intended to be merely exemplary and numerous variations and modifications will be apparent to those skilled in the art. All such variations and modifications are intended to be within the scope of the present invention as defined in the appended claims.

Where examples presented herein involve specific combinations of method acts or system elements, it should be understood that those acts and those elements may be combined in other ways to accomplish the same objective of x-ray inspection. Additionally, single device features may fulfill the requirements of separately recited elements of a claim. The embodiments of the invention described herein are intended to be merely exemplary; variations and modifications will be apparent to those skilled in the art. All such variations and modifications are intended to be within the scope of the present invention as defined in any appended claims.

What is claimed is:

1. A method for characterizing regions within an inspected object wherein at least one of a lower-Z scattering material and a higher-Z scattering material lies along a single line of sight, the method comprising:
   a. scanning the inspected object with penetrating radiation emitted by a source characterized by an energy distribution;
   b. detecting penetrating radiation scattered by the inspected object in a manner generating a first detector signal that distinguishes between materials of higher and lower effective atomic number under a first set of conditions with respect to the energy distribution of the penetrating radiation;
   c. detecting penetrating radiation scattered by the inspected object in a manner generating a second detector signal that distinguishes between materials of higher and lower effective atomic number under a second set of conditions with respect to the energy distribution of the penetrating radiation;
   d. generating a differential image based on a function of the first and the second detector signals; and
   e. determining placement of materials of lower Z and higher Z within a single line of sight relative to the source, based at least on the differential image.

2. A method in accordance with claim 1, wherein scanning the inspected object with penetrating radiation characterized by an energy distribution comprises sequentially scanning the inspected object with penetrating radiation characterized by a first energy distribution and a second energy distribution.

3. A method in accordance with claim 1 or claim 2, further comprising a step of ascertaining relative placement of a lower-Z region with respect to a higher-Z region within the inspected object based at least on values of respective regions within the differential image.

4. A method in accordance with claim 1 or claim 2, wherein respective regions are defined, in whole or in part, based upon segmentation.

5. A method in accordance with claim 1 or claim 2, wherein the penetrating radiation is x-ray radiation.

6. A system for characterizing regions within an inspected object, the system comprising:
   a. a source of penetrating radiation for generating a beam of penetrating radiation;
   b. a scanner for scanning the penetrating radiation across the inspected object;
   c. an energy discriminating means for distinguishing scattered penetrating radiation detected under a first set of conditions with respect to an energy distribution of scattered penetrating radiation and under a second set of conditions with respect to an energy distribution of scattered penetrating radiation;
   d. an image generator for generating a first image based on a function of the radiation detected under only one of the first and second set of conditions with respect to the energy distribution; and
   e. a difference image generator for generating a differential image based on a function of the radiation detected under the first set of conditions and the radiation detected under the second set of conditions with respect to the energy distribution.

7. A system in accordance with claim 6, wherein the energy discriminating means comprises
   a. a first detector characterized by a first response distribution as a function of detected energy and
   b. a second detector characterized by a second response distribution as a function of detected energy.

8. A system in accordance with claim 6, wherein the source of penetrating radiation is an x-ray tube.

9. A system in accordance with claim 7, wherein the first and second detectors are disposed on respective sides of the source of penetrating radiation.

10. A system in accordance with claim 7, wherein the first and second detectors are disposed on each side of the source of penetrating radiation.

* * * * *